United States Patent
Keating et al.

(10) Patent No.: US 9,855,031 B2
(45) Date of Patent: Jan. 2, 2018

(54) SUTURE DELIVERY SYSTEM

(71) Applicant: NEOSURGICAL LIMITED, Galway (IE)

(72) Inventors: Ronan Keating, Galway (IE); Gerard Rabbitte, Galway (IE); Barry Russell, Kildare (IE)

(73) Assignee: NEOSURGICAL LIMITED, Parkmore, Galway (IE)

( * ) Notice: Subject to any disclaimer, the term of this patent is extended or adjusted under 35 U.S.C. 154(b) by 367 days.

(21) Appl. No.: 13/688,005

(22) Filed: Nov. 28, 2012

(65) Prior Publication Data
US 2013/0090670 A1    Apr. 11, 2013

Related U.S. Application Data

(63) Continuation-in-part of application No. 13/641,014, filed as application No. PCT/EP2011/055862 on Apr. 13, 2011.
(Continued)

(30) Foreign Application Priority Data

Dec. 17, 2010    (GB) .................................... 1021479.9

(51) Int. Cl.
*A61B 17/04*    (2006.01)
*A61B 17/34*    (2006.01)
(Continued)

(52) U.S. Cl.
CPC ...... *A61B 17/0469* (2013.01); *A61B 17/0401* (2013.01); *A61B 17/0482* (2013.01);
(Continued)

(58) Field of Classification Search
CPC ............ A61B 17/0482; A61B 17/0401; A61B 17/3421; A61B 17/3417; A61B 2017/3454; A61B 17/0469; A61B 2017/0475; A61B 2017/0445; A61B 2017/0446; A61B 2017/0448; A61B 17/0462; A61B 2017/0409; A61B 2017/0496; A61B 2017/0403; A61B 2017/0404; A61B 2017/0406; A61B 2017/0408; A61B 2017/0411; A61B 2017/0412; A61B 2017/0414; A61B 2017/0417; A61B 2017/0419; A61B 2017/042;
(Continued)

(56) References Cited

U.S. PATENT DOCUMENTS 3,409,014 A    11/1968    Grant
5,330,437 A    7/1994    Durman
(Continued)

FOREIGN PATENT DOCUMENTS

WO    2004030515 A2    4/2004
WO    2005122911 A1    12/2005

*Primary Examiner* — Tuan V Nguyen
*Assistant Examiner* — Chima Igboko
(74) *Attorney, Agent, or Firm* — Schwabe Williamson & Wyatt, PC

(57) ABSTRACT

A suture delivery system is described. The system includes an anchor and a cooperating driver, the driver facilitating a delivery of the anchor into the abdominal cavity. The system allows for the deployment of a suture internally into an abdominal wall.

33 Claims, 12 Drawing Sheets

Related U.S. Application Data

(60) Provisional application No. 61/323,367, filed on Apr. 13, 2010.

(51) Int. Cl.
*A61B 17/06* (2006.01)
*A61B 17/00* (2006.01)

(52) U.S. Cl.
CPC ...... *A61B 17/0491* (2013.01); *A61B 17/3421* (2013.01); *A61B 17/3423* (2013.01); *A61B 17/06061* (2013.01); *A61B 17/06128* (2013.01); *A61B 17/3496* (2013.01); *A61B 2017/00477* (2013.01); *A61B 2017/00637* (2013.01); *A61B 2017/00663* (2013.01); *A61B 2017/00902* (2013.01); *A61B 2017/0409* (2013.01); *A61B 2017/0414* (2013.01); *A61B 2017/0417* (2013.01); *A61B 2017/0437* (2013.01); *A61B 2017/0445* (2013.01); *A61B 2017/0464* (2013.01); *A61B 2017/06042* (2013.01); *A61B 2017/3441* (2013.01); *A61B 2017/3466* (2013.01)

(58) Field of Classification Search
CPC .... A61B 2017/0427; A61B 2017/0438; A61B 2017/045; A61B 17/0451; A61B 2017/0456; A61B 2017/0458; A61B 17/0459; A61B 2017/0461; A61B 2017/0464
USPC ......................................................... 606/144
See application file for complete search history.

(56) References Cited

U.S. PATENT DOCUMENTS

| | | |
|---|---|---|
| 5,443,484 A | 8/1995 | Kirsch et al. |
| 5,460,170 A | 10/1995 | Hammnerslag |
| 5,478,345 A | 12/1995 | Stone et al. |
| 5,514,133 A | 5/1996 | Golub et al. |
| 5,618,309 A | 4/1997 | Green et al. |
| 5,634,937 A | 6/1997 | Mollenauer et al. |
| 5,672,168 A | 9/1997 | de la Torre et al. |
| 5,716,369 A | 2/1998 | Riza |
| 5,827,299 A | 10/1998 | Thomason et al. |
| 5,830,125 A | 11/1998 | Scribner et al. |
| 5,891,159 A | 4/1999 | Sherman et al. |
| 5,906,577 A | 5/1999 | Beane et al. |
| 5,948,002 A | 9/1999 | Bonutti |
| 5,954,732 A | 9/1999 | Hart et al. |
| 6,059,800 A | 5/2000 | Hart et al. |
| 6,143,004 A | 11/2000 | Davis et al. |
| 6,168,598 B1 | 1/2001 | Martello |
| 6,190,396 B1 | 2/2001 | Whitin et al. |
| 6,203,554 B1 | 3/2001 | Roberts |
| 6,383,208 B1 | 5/2002 | Sancoff et al. |
| 6,440,063 B1 | 8/2002 | Beane et al. |
| 6,478,028 B1 | 11/2002 | Paolitto et al. |
| 6,488,692 B1 | 12/2002 | Spence et al. |
| 6,589,167 B1 | 7/2003 | Shimomura et al. |
| 6,610,071 B1 | 8/2003 | Cohn et al. |
| 6,770,084 B1 | 8/2004 | Bain et al. |
| 7,344,495 B2 | 3/2008 | Ravikumar et al. |
| 7,393,322 B2 | 7/2008 | Wenchell |
| 7,850,600 B1 | 12/2010 | Piskun |
| 7,909,804 B2 | 3/2011 | Stats |
| 7,951,117 B2 | 5/2011 | Wingardner et al. |
| 7,967,748 B2 | 6/2011 | Kistler et al. |
| 8,657,740 B2 | 2/2014 | Bonadio et al. |
| 8,727,974 B2 | 5/2014 | Kasvikis |
| 8,734,336 B2 | 5/2014 | Bonadio et al. |
| 8,795,161 B2 | 8/2014 | Carter |
| 8,961,406 B2 | 2/2015 | Ortiz et al. |
| 2002/0111638 A1 | 8/2002 | Whitin et al. |
| 2003/0010346 A1 | 1/2003 | Paolitto et al. |
| 2003/0153921 A1 | 8/2003 | Stewart et al. |
| 2003/0158562 A1 | 8/2003 | Feigl |
| 2004/0015185 A1 | 1/2004 | Ewers et al. |
| 2004/0087833 A1 | 5/2004 | Bauer et al. |
| 2004/0092965 A1 | 5/2004 | Parihar |
| 2004/0138683 A1* | 7/2004 | Shelton ............ A61B 17/0401 606/151 |
| 2004/0167543 A1 | 8/2004 | Mazzochi et al. |
| 2004/0167546 A1* | 8/2004 | Saadat et al. ............ 606/144 |
| 2004/0176786 A1 | 9/2004 | Edoga et al. |
| 2004/0254593 A1 | 12/2004 | Fallin et al. |
| 2005/0065535 A1 | 3/2005 | Morris et al. |
| 2005/0215863 A1 | 9/2005 | Ravikumar et al. |
| 2005/0222582 A1 | 10/2005 | Wenchell |
| 2005/0251206 A1* | 11/2005 | Maahs et al. ............ 606/232 |
| 2005/0283192 A1* | 12/2005 | Torrie ............ A61B 17/0401 606/228 |
| 2006/0178702 A1* | 8/2006 | Pierce ............ A61B 17/0401 606/232 |
| 2006/0217762 A1* | 9/2006 | Maahs et al. ............ 606/213 |
| 2006/0247500 A1 | 11/2006 | Voegele et al. |
| 2007/0021781 A1 | 1/2007 | Jervis et al. |
| 2007/0032823 A1 | 2/2007 | Tegg |
| 2007/0049929 A1* | 3/2007 | Catanese et al. ............ 606/46 |
| 2007/0112425 A1* | 5/2007 | Schaller et al. ............ 623/2.37 |
| 2007/0225719 A1* | 9/2007 | Stone ............ A61B 17/0401 606/232 |
| 2008/0058584 A1* | 3/2008 | Hirotsuka ............ A61B 17/0401 600/37 |
| 2008/0097485 A1 | 4/2008 | Shpaichler et al. |
| 2008/0140092 A1* | 6/2008 | Stone et al. ............ 606/144 |
| 2008/0140093 A1* | 6/2008 | Stone et al. ............ 606/144 |
| 2008/0208131 A1 | 8/2008 | Powers et al. |
| 2008/0243148 A1* | 10/2008 | Mikkaichi et al. ............ 606/144 |
| 2008/0255519 A1 | 10/2008 | Piskun et al. |
| 2008/0294001 A1 | 11/2008 | Surti |
| 2009/0036745 A1 | 2/2009 | Bonadio et al. |
| 2009/0069823 A1 | 3/2009 | Foerster et al. |
| 2009/0093683 A1 | 4/2009 | Richard et al. |
| 2009/0157105 A1 | 6/2009 | Zung et al. |
| 2009/0221966 A1 | 9/2009 | Richard |
| 2009/0227843 A1 | 9/2009 | Smith et al. |
| 2009/0287308 A1* | 11/2009 | Davis et al. ............ 623/13.12 |
| 2009/0292176 A1 | 11/2009 | Bonadio et al. |
| 2009/0326564 A1 | 12/2009 | White et al. |
| 2010/0004665 A1 | 1/2010 | Hong et al. |
| 2010/0010512 A1* | 1/2010 | Taylor et al. ............ 606/144 |
| 2010/0023026 A1* | 1/2010 | Zeiner et al. ............ 606/144 |
| 2010/0030262 A1 | 2/2010 | McLean et al. |
| 2010/0063364 A1 | 3/2010 | Bonadio et al. |
| 2010/0063452 A1 | 3/2010 | Edelman et al. |
| 2010/0069930 A1 | 3/2010 | Roslin et al. |
| 2010/0076462 A1* | 3/2010 | Bakos et al. ............ 606/146 |
| 2010/0081880 A1 | 4/2010 | Widenhouse et al. |
| 2010/0130824 A1 | 5/2010 | Piskun |
| 2010/0222643 A1 | 9/2010 | Piskun et al. |
| 2010/0262166 A1* | 10/2010 | Boraiah ............ A61B 17/0057 606/148 |
| 2010/0268035 A1 | 10/2010 | Oberlander et al. |
| 2010/0312063 A1 | 12/2010 | Hess et al. |
| 2011/0270194 A1 | 11/2011 | Piskun |

\* cited by examiner

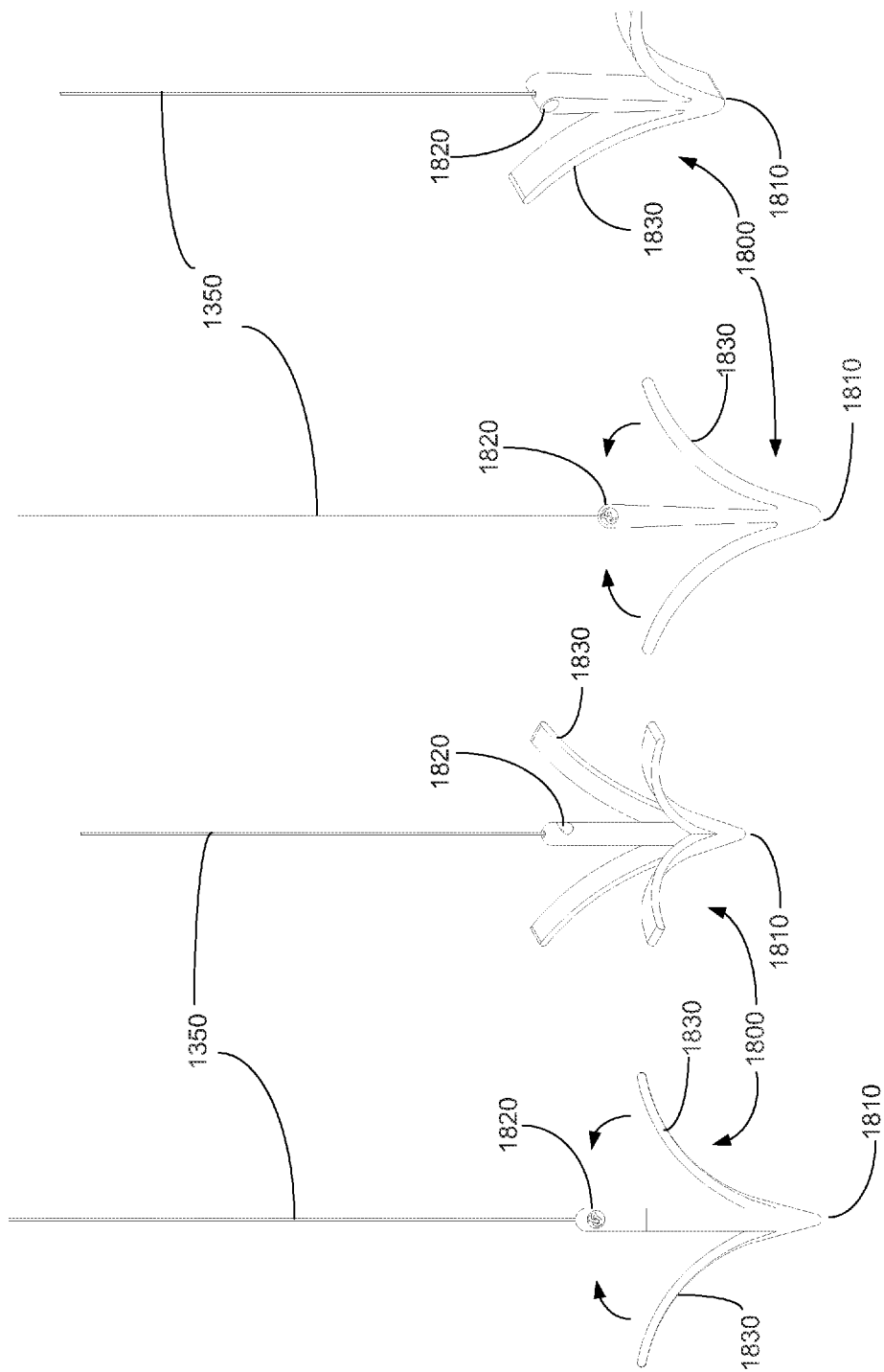

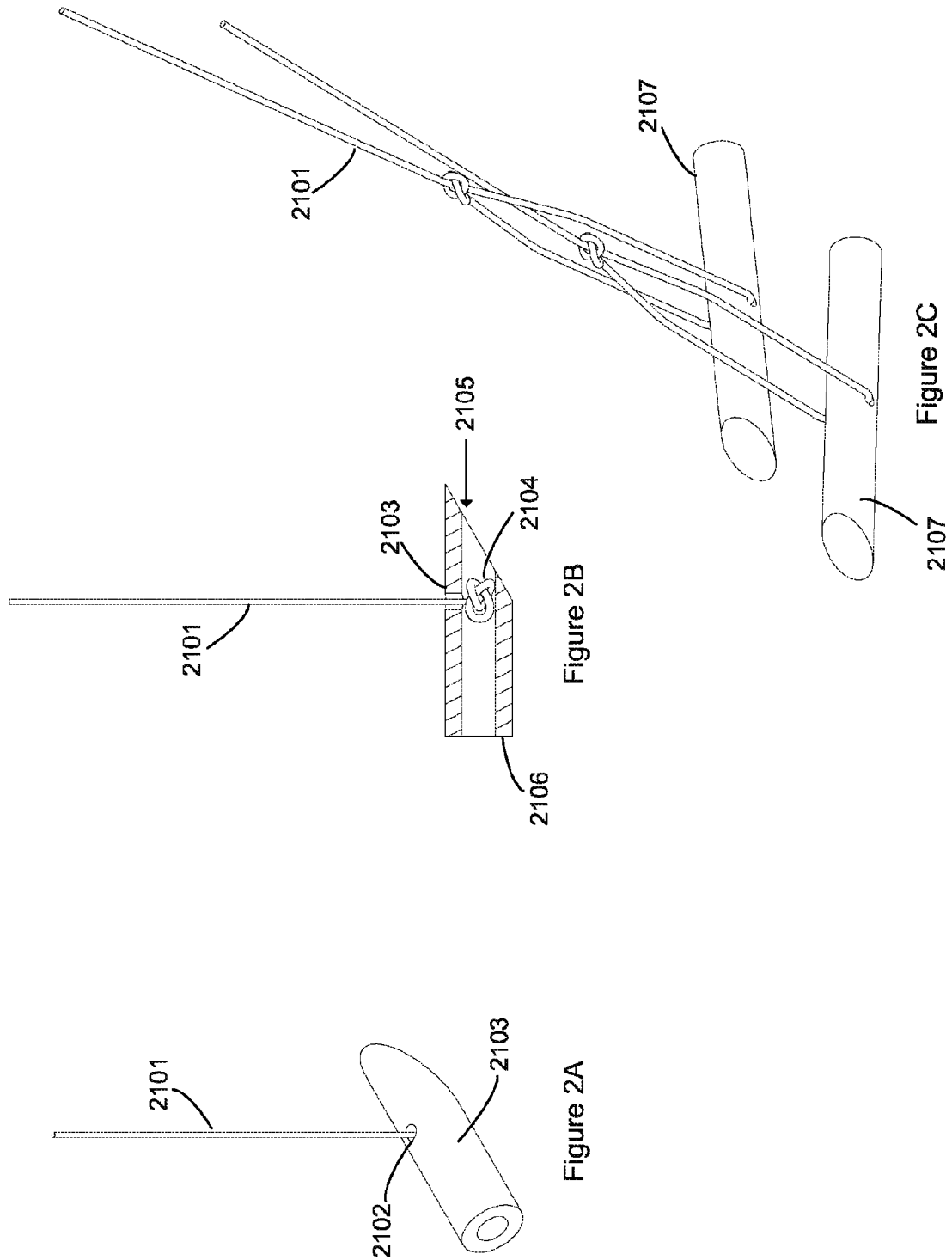

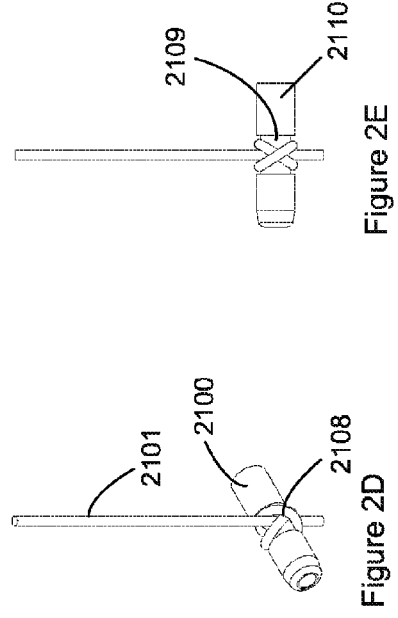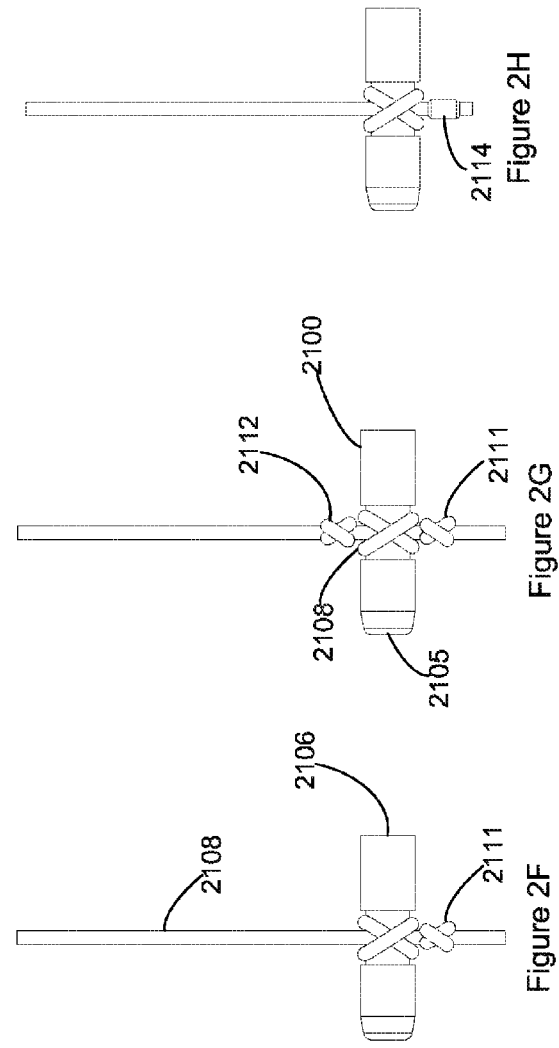

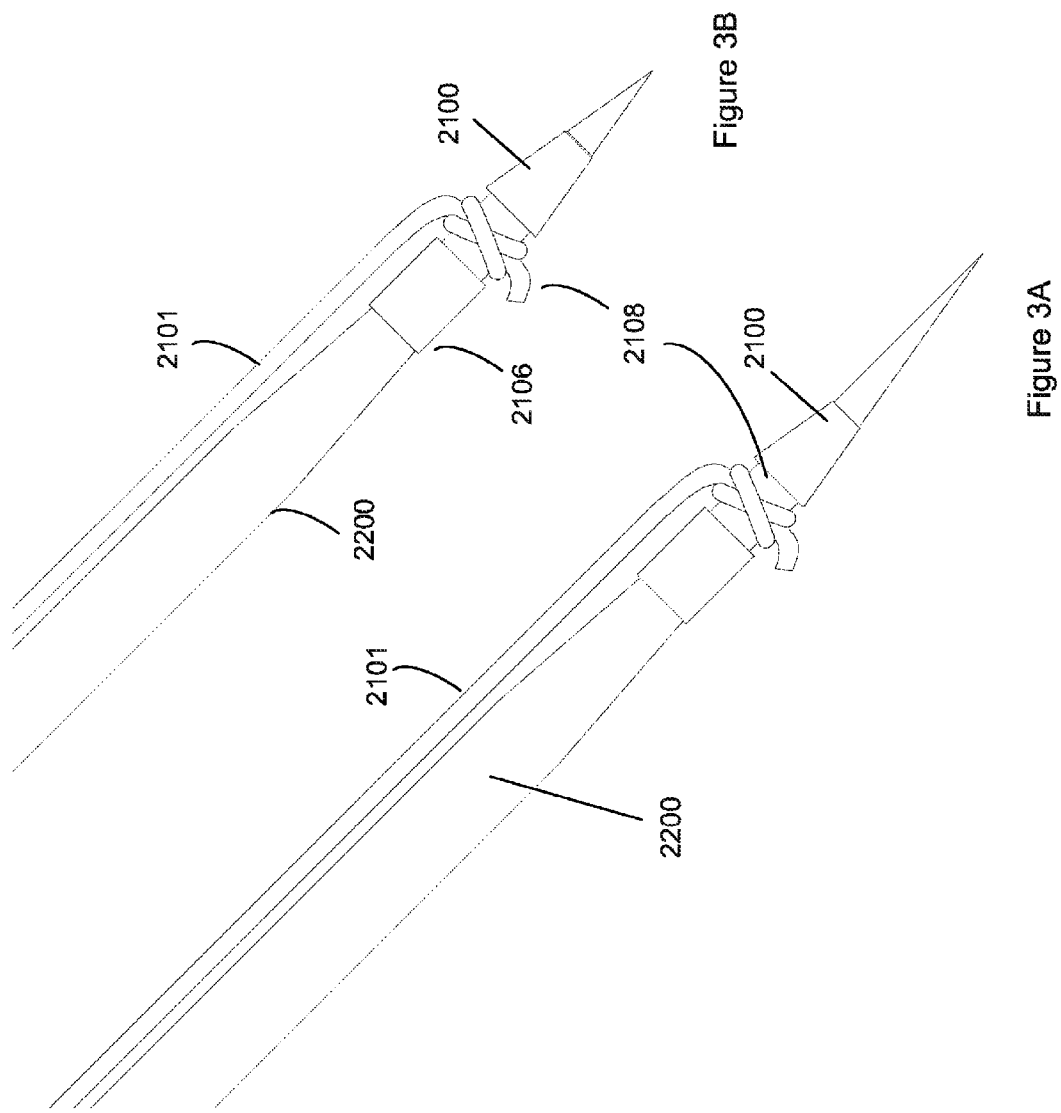

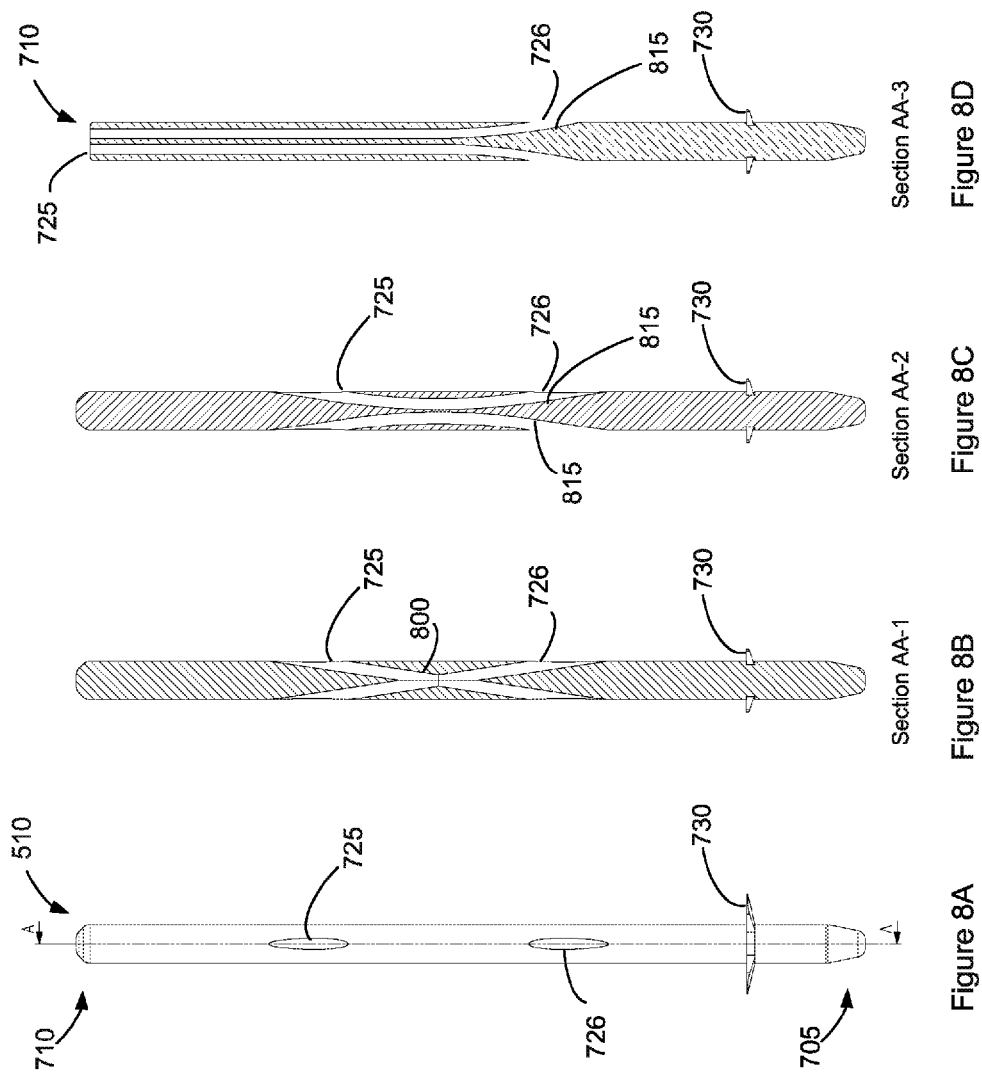

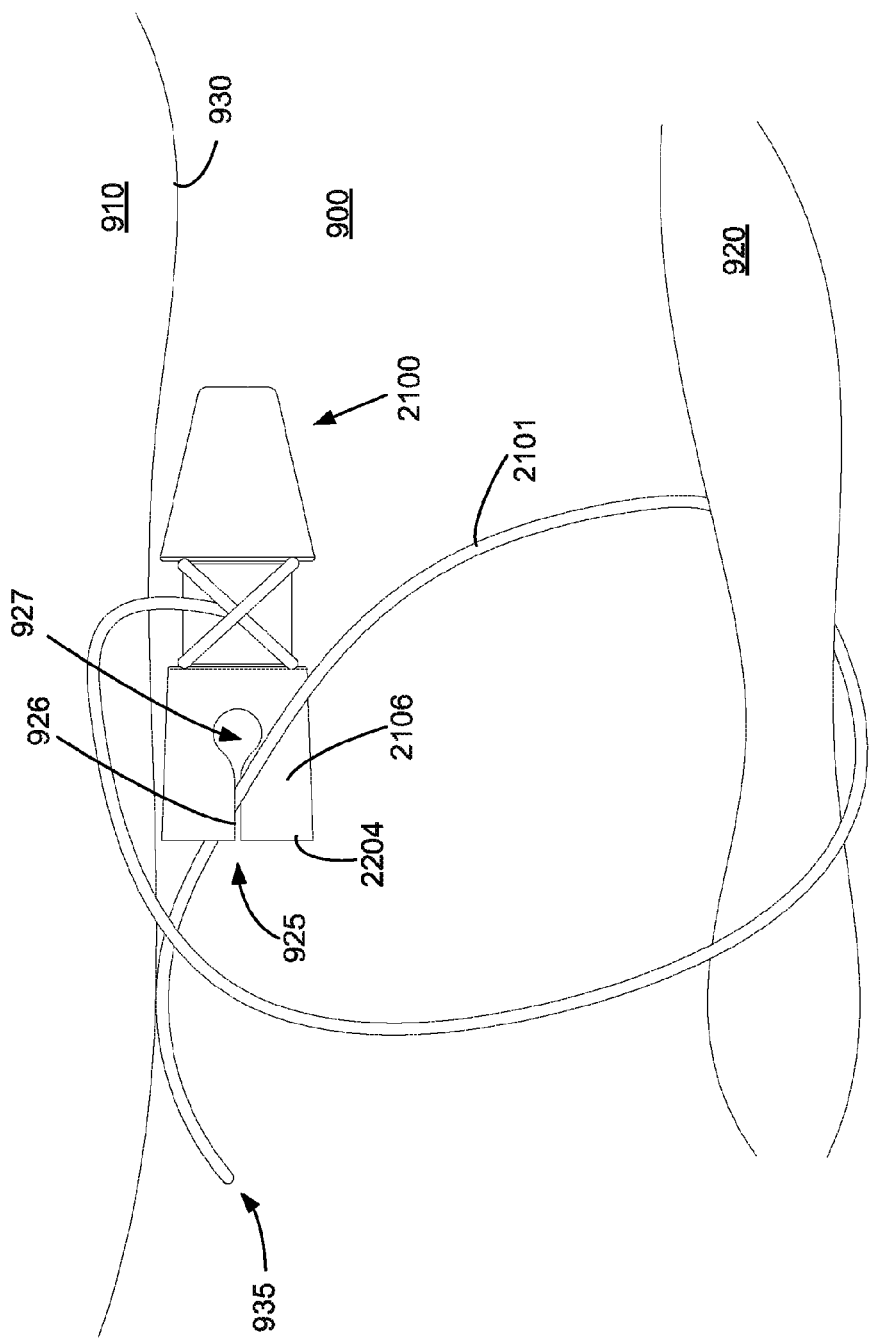

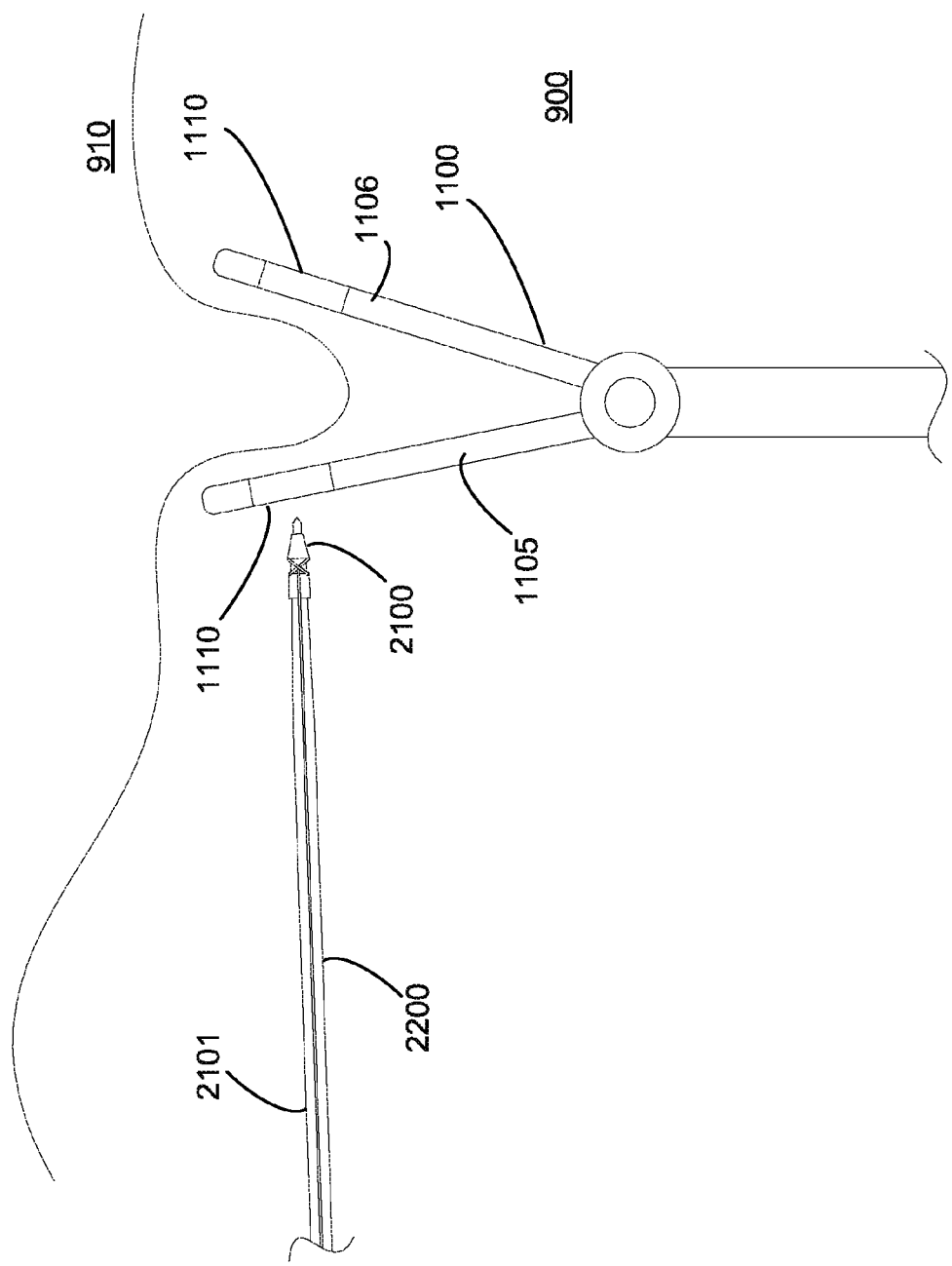

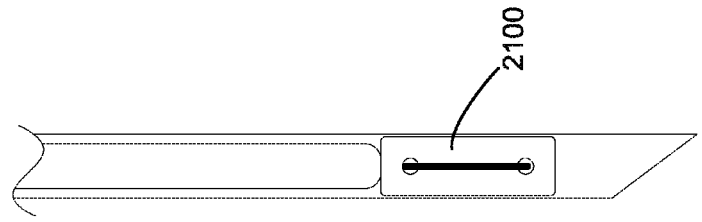
Figure 12E
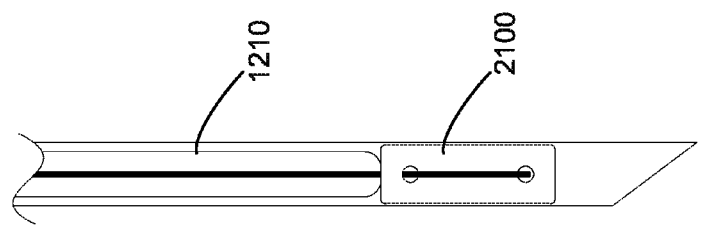
Figure 12D
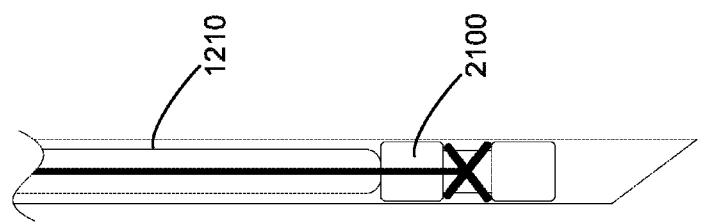
Figure 12C
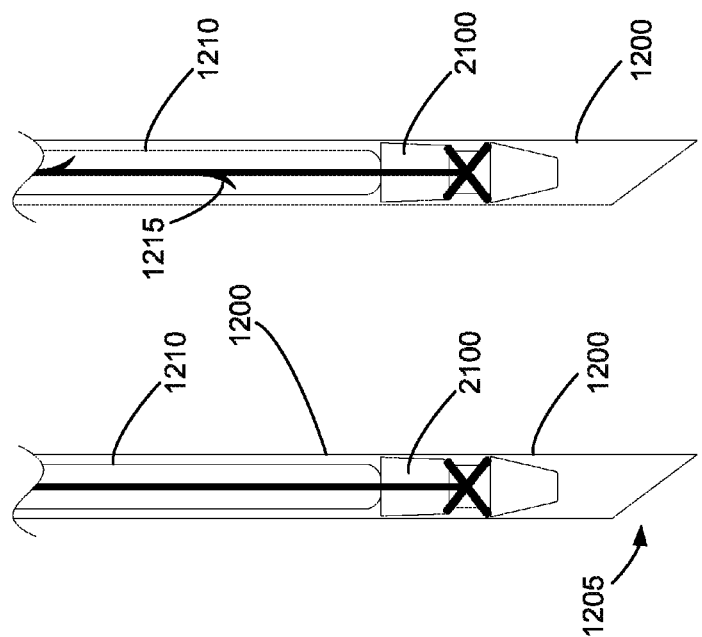
Figure 12B
Figure 12A

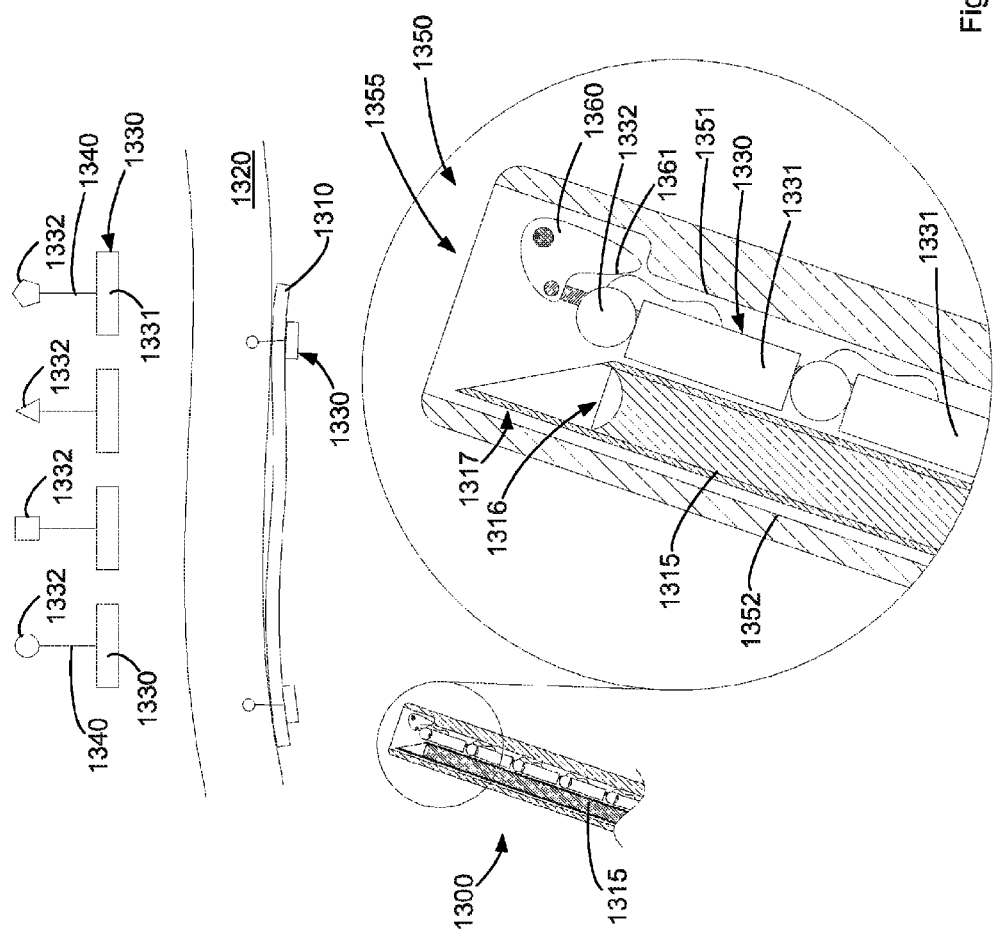

SUTURE DELIVERY SYSTEM

CROSS REFERENCE TO RELATED APPLICATIONS

The present application is a Continuation-in-Part of and claims priority to U.S. patent application Ser. No. 13/641,014, filed Oct. 12, 2012, which is the US National Phase of PCT/EP2011/055862, filed Apr. 13, 2011, which claims priority to U.S. Provisional Patent Application No. 61/323,367, filed Apr. 13, 2010, the entire specifications of which are hereby incorporated by reference in their entirety for all purposes.

FIELD OF THE INVENTION

The present invention relates to a suture delivery system. In one configuration it relates to a suture delivery system which operably provides for deployment of an anchoring system which is usefully employed in laparoscopic surgery. In another configuration it relates to a suture delivery system which operably provides a closure system which is usefully employed in laparoscopic surgical procedures.

BACKGROUND

There are difficulties sometimes associated with the closure of the trocar wound site for example, in laparoscopic procedures. There are difficulties in particular in finding the fascia layer through which a suture must be passed to ensure good and adequate port site closure.

With deeper port sites, such as with an obese patient, it is often more difficult for the surgeon to gain deep access to the fascial layer to securely place a suture therein. In certain instances it may be necessary to cut open the wound to accurately place a suture fixation on the inner fascia layer.

The consequences of inadequate closure may be serious. For example, the patient may be subject to an early or late onset hernia, bowel stricture and/or bleeding from the port site. All of these complications have varying associated morbidities up to and including fatalities in serious undetected bowel strictures. The rate of port site herniation is widely published to be up to 3% for the normal population and double this for the obese cohort.

There are therefore a number of problems with current methods of trocar port site closure that need to be addressed, particularly for the obese patient.

There are further difficulties in anchoring or otherwise securing laparoscopic surgical devices relative to a laparoscopic surgical port, in particular with Hasson type ports. Suture stays can be difficult to manage during Hasson trocar olive fixation and can become tangled when removing or adjusting the trocar. These problems also need to be addressed in order to ensure an efficient workflow for the surgeon.

These and other problems are also found in non-laparoscopic surgical techniques where there is a desire to deliver suture to a wound site.

SUMMARY

These needs and others are addressed in accordance with the present teaching which provides a suture delivery system for deployment of a suture and anchor to enable port site closure subsequent to a laparoscopic surgical procedure. In one configuration the suture delivery system is used for anchoring purposes during a surgical procedure.

These and other features of the present teaching will be better understood with reference to the drawings which follow which are provided to assist in an understanding of the present teaching and are not to be construed as limiting in any fashion.

BRIEF DESCRIPTION OF THE DRAWINGS

The present teaching will now be described with reference to the accompanying drawings in which:

FIGS. 1A to 1D show examples of anchors that may be provided in accordance with the present teaching;

FIGS. 2A through 2H show examples of anchors that may be provided in accordance with the present teaching;

FIG. 3A and 3B show examples of an anchor and cooperating driver in accordance with the present teaching.

FIG. 8A is another view of the guide of FIG. 7.

FIG. 8B is a section through one example of a guide per the teaching of FIG. 8A.

FIG. 8C is a section through one example of a guide per the teaching of FIG. 8A.

FIG. 8D is a section through one example of another guide.

FIG. 9 shows an example of how an anchor may be used to effect movement of an organ in accordance with the present teaching.

FIG. 11 shows an example of a tissue grasper that may be used with the anchor of FIG. 9 or 10 in accordance with the present teaching.

FIGS. 12A to 12E show example of anchor/driver combinations in use with other forms of guides to that described with reference to FIG. 8.

FIG. 13 shows an arrangement whereby a plurality of anchors can be delivered in a sequential fashion.

DETAILED DESCRIPTION OF THE DRAWINGS

Figure 4:
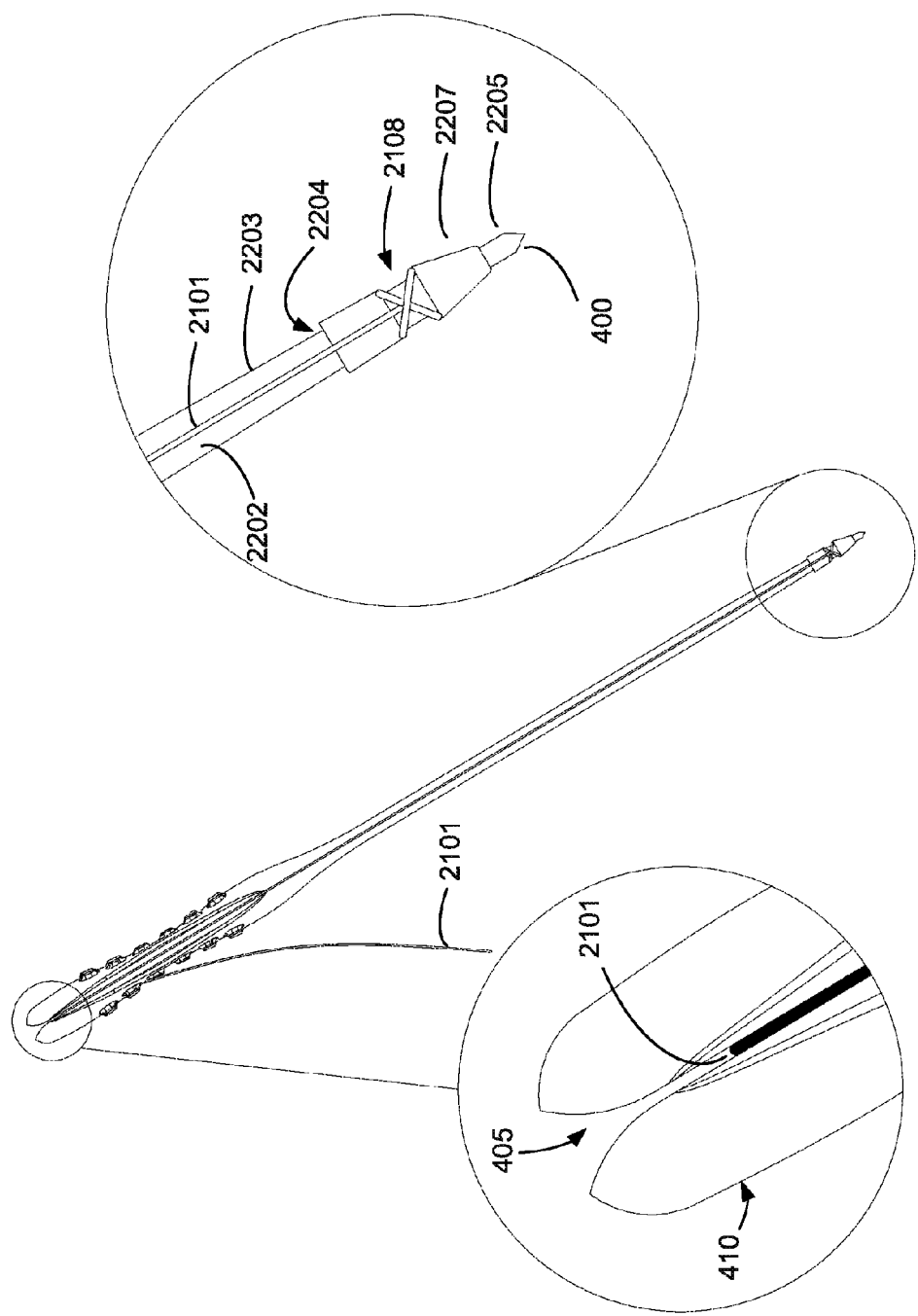
FIG. 4 is another example of a driver and anchor combination.

The teaching of the present invention will now be described with reference to exemplary embodiments thereof which are provided to assist with an understanding of the invention and are not to be construed as limiting in any way. It will be appreciated that modifications can be made to the exemplary arrangements which follow without departing from the scope of the invention which is only to be limited insofar as is deemed necessary in the light of the appended claims.

Within the context of the present teaching a suture delivery system advantageously allows for the delivery of suture within an abdominal cavity of the patient. It will be appreciated that the following discussion regarding the specifics of the abdominal cavity and abdominal wall should not be construed as limiting in that a system provided in accordance with the present teaching may be used with other types of tissue including but not limited to organs, bones or the like. The use of a suture delivery system per the present teaching can be used for one or more of anchoring laparoscopic surgical equipment, assisting in the moving of internal organs to allow a surgeon access to a surgical site, or closure of a wound post completion of a surgical procedure. In such a latter configuration, where the suture is coupled to an anchor, as the suture is passed through the abdominal wall and is held within the wall by the anchors that will remain deployed within the abdominal cavity, a subsequent tightening of the sutures will cause the sides of the incision, or break in the abdominal cavity to be brought together to close the wound. The adoption of such a technique will advantageously require the use of bioabsorbable anchors, as the anchors will remain within the abdominal cavity during the healing process prior to their ultimate disintegration.

In a further embodiment the anchors may be made from a ferromagnetic material so that a magnet could be passed down a trocar and the anchors would be attracted to and adhere to the magnet, allowing them to be drawn out through the trocar. The advantage of this approach is that direct visualisation may not be necessary. However, the anchors would need to be removed prior to tying the suture in a loop. Alternatively the anchors may be themselves magnets and a ferromagnetic pick up device could be employed through the trocar to pick up the anchors.

In accordance with an aspect of the present teaching an anchor is coupled to the suture. The anchor may then be delivered to the surgical site through co-operation of the anchor with a driver tool. The driver engages with the anchor and is then used to deliver the anchor and its associated suture through to the abdominal cavity. A tensionsing of the suture will then allow for a retraction of the anchor against an inner part of the abdominal wall, where it then provides an anchoring function. In providing for delivery of the anchor, the present teaching usefully provides in one embodiment, features on one or either of the anchor or driver which serves to minimise rotation of the anchor about the needle driver during delivery. One arrangement whereby such rotation could be prevented is by making the profile of the anchor oval and engaging it with a flat on the driver. It will be appreciated that various shapes may be employed to achieve a non-rotate feature, and that the example given is not limiting. Such a non-rotate feature may be usefully employed in an application where it is required to orientate the angled cut of a driver in a given orientation.

The driver may be used in combination with a needle guide channel such as those described in our co-pending application U.S. Ser. No. 13/975,599, the content of which is incorporated herein by reference. As described therein, in use, when the driver is presented into a needle entry port it moves within the channel until such time as it meets with the anchor that is located within the channel. It then drives the anchor through the channel until it exits through an exit port where it extends into the abdominal cavity.

In this configuration, to allow the driver to pass through an arcuate needle channel, it is desirably at least partially flexible.

FIG. 1 shows example of anchors 1800 that may be employed within the present teaching. In each of the exemplary arrangements the anchors comprise a head portion 1810 and a suture coupling portion 1820 at opposing ends of the anchor. Two or more barbs 1830 are also provided. The barbs are at least partially flexible and are orientated that in the absence of an applied force thereon will extend outwardly from the head 1810. When being driven through a needle channel or the abdominal wall itself, the barbs 1830 are displaced inwardly to be substantially parallel with the major longitudinal axis of the anchor—that axis extending from the head 1810 to the suture coupling portion 1820. In this way the cross sectional area of the anchor is reduced when it is passing through the needle guide channel but once exiting from the channel the barbs will extend outwardly. On tensioning the suture, the barbs will then serve to anchor against the abdominal wall and secure the olive to the abdominal wall.

While the head portion 1810 is illustrated here with a radiused tip, this is not intended to be limiting, as the head portion may feature any number of needle tip configurations.

The suture/anchor assembly may consist of a length of bioabsorbable suture attached to a length of bioabsorbable tubing in one embodiment such that the assembly is t-shaped. The suture may be a braided suture made from a bioabsorbable polymer such as PGA for example. For fascial layer closure a USP size 0 suture is preferred. This material is ideally suited to an application where the suture maintains approximately 50% of its strength after two weeks. However it will be appreciated that the suture material may be changed depending on strength or mass loss requirements of the specific application.

In the arrangement of FIG. 1, the anchor may be deployed using a driver (not shown). In such a deployment, the driver will typically engage with or couple to the suture coupling portion 1820. In one configuration the driver comprises a hollow drive tip which is receivable onto the suture coupling portion 1820—the suture coupling portion being at least partially received into the hollow tip. In this configuration the mating of the anchor with the driver provides an integrated anchor delivery tool where the head 1810 of the anchor is used to pierce the abdominal wall upon application of a force using the driver. The barbs may retract to align along an outer surface of the driver during delivery.

In such a configuration the suture 1350 may be passed internally within the driver—requiring the body of the driver to be substantially hollow. In another configuration the suture will pass along the outer surface of the driver.

The anchor of FIG. 1 is suspended at one end of the anchor from the suture 1350 so that it hangs vertically from the suture. In another configuration, suture is coupled to the anchor in a way that causes the anchor to extend laterally or horizontally from the suture. Such a configuration effectively provides a T-bar arrangement whereby the suture forms the body of the T and the anchor the horizontal member that is coupled to the body. Examples of such an arrangement will be described with reference to FIG. 2.

Such an arrangement may be deployed using a braided suture which has the advantage of securely holding a knot and is well suited to the construction method illustrated in 2A and 2B. Here the anchor 2103 is formed from a short length of PGLA tubing and has a hole 2102 made in its side wall. The suture 2101 is threaded through this hole and knotted with a double overhand knot. The knot is then pulled back into the main lumen of the tubing, the knot being too large to come through the hole 2102 on the side wall. It will be appreciated that while a double overhand knot is used in this embodiment the disclosure of such is not intended to limit the type of knot used. Additionally braided suture is not as prone to taking a shape set when wound tightly on a spool as monofilament is, making braided suture a preferred option on devices which entail the suture being wound on a spool.

In an application where anchors are not delivered through the abdominal wall, a monofilament suture could be used. Polydioxanone (PDS) and Poly(glycolide-co-caprolactone) (Poliglecaprone 25) are examples of such materials. A disadvantage of monofilament suture is its reduced knot strength when compared to a comparably sized braided suture. An assembly employing monofilament suture may include a larger diameter suture, or be crimped into the anchor if the anchor is a stainless steel option. Where the suture is attached to a bioabsorbable anchor there is the option of heat welding the two components together or passing the suture through a narrow hole in the anchor and heat forming the tip of the suture, so that it does not pass back through the hole. Another option would be to place multiple barbs on the suture so that the suture itself acts as an anchor. An example of such suture will be described later.

The anchor in this configuration consists of an extruded tube. The hole in the side wall is sized to suit the suture diameter and may be disposed at the centre of the extruded length. The tubing material in an exemplary arrangement is Poly(L-lactide-co-glycolide) (PLGA) but could be made from any ratios of the following materials Poly(L-lactide-co-glycolide) (PLGA), Polylactic acid (PLA), Polyglycolide (PGA), Polydioxanone (PDS), Polycaprolactone (PCL). In one example of use, the sutures and anchors may be composed of a fast degrading polymer. In another embodiment the sutures and anchors may be composed of a slow degrading polymer. In another variant the anchors may have an additional coating of Polylactic acid (PLA) or Polycaprolactone (PCL) or a co-polymer blend of these polymers in order to vary the degradation profile. In another case, the degree of crystallisation of the polymer composition of the anchors may be altered through heating and cooling treatments to change its mechanical properties.

FIG. 2 shows various examples of anchors that may be deployed in accordance with the present teaching. In the arrangement of FIG. 2A a suture 2101 is passed through an aperture 2102 in the body of the anchor 2103. As shown in the section view of FIG. 2B, a knot 2104 may then be tied to retain the suture relative to the anchor. The anchor body 2103 is desirably hollow to allow both for location of the knot within the body, but also to allow for engagement of a driver with the anchor to enable its presentation through the abdominal wall into the abdominal cavity. A front end or leading surface 2105 is chamfered or otherwise sharpened to provide a driving surface to facilitate the passage through the abdominal wall. The back end or trailing surface 2106 is desirably the end that engages with the driver, not shown. While not shown in FIG. 2B, it will be appreciated that an additional aperture may be provided in the body of the anchor whereby suture may be reintroduced into the anchor body and then travel out of the back end 2106 of the anchor. Such an implementation would be particularly useful in combination with a hollow driver whereby the suture could then pass directly into the driver. This could be particularly useful in the context of use of barbed suture where there is a desire to minimise the exposure of the barbs to the tissue until such time as deployment is required.

FIG. 2C shows an alternative coupling arrangement for facilitating tethering of the anchor to suture. In this configuration the suture passes through the body 2107 of the anchor—first and second apertures are provided to facilitate this passage. On threading the suture through the body it may then be tied against itself to retain the anchor within a loop. First and second anchors could be retained against one another by passing a first anchor through the loop formed for the second. In the embodiment illustrated the body of the anchor is solid, but this is not intended to be limiting.

FIGS. 2D and 2E shows a further arrangement whereby suture 2101 is tied around an outer surface of an anchor 2100 in a knot 2108. In this arrangement the knot is located within a recessed portion 2109 of the outer body of the anchor. In this way the physical formation of the knot does not project substantially beyond the major surface 2110 of the anchor. It will be understood that the anchor is delivered in direction that is substantially parallel to the major axis of the body and that the recessed portion prevents lateral movement of the knot as it is driven through tissue.

As shown in FIG. 2F, the location of the knot 2108 to the anchor may be more closely secured by provision of a second knot 2111 below the anchor. Further securing could be facilitated by a third knot 2112 above the anchor such as shown in FIG. 2G. Another alternative is a heat formed flat 2114 provided such as the example of FIG. 2H. In an alternative embodiment, not shown, the end of the suture could be heat stamped. It will be appreciated that heat forming a braided material in this fashion will produce a flared end to the suture, which could be usefully employed to prevent the end of the suture pulling through the knot. In a further embodiment, not illustrated here, the knot or a portion of the knot could be dipped or coated in liquid bioabsorbable polymer for example polyglycolide, poly(d-lactide), poly(l-lactide), poly(dl-lactide), polycaprolactone or copolymers of those listed. Alternately the end of the suture could be dipped to form a stiff portion in a similar manner to an aglet on a shoe lace, which would prevent this portion form being pulled into the knot when tension is applied to the suture, avoiding knot failure.

FIGS. 2D-2H illustrate assemblies where the suture is attached to the anchor with a constrictor knot. It will be appreciated however, that other knots could be usefully employed to achieve a similar result, examples of which would be a boa knot, double overhand, strangle knot or double constrictor. This list is not intended to be limiting and the selection of knot is based on end requirements like knot security and knot profile.

The knot of FIGS. 2D-2E may be further secured by pre-tensioning the knot. This may be achieved by making the knot, securing one end of the suture, and to the other end applying a weight. The weight used could be in the range 0.5 kg-2 kg, and more specifically 1 kg for the illustrated embodiment. This range is not intended to be limiting as a number of factors influence knot security, for example the suture material, braid construction, knot selection or the presence of adjacent knots or flats as illustrated in FIGS. 2F-H.

In each of the above examples of FIG. 2 the anchor is substantially hollow so as to allow presentation of a driver into an inner volume of the anchor. In this way the anchor will be arranged collinearly with the longitudinal axis of the driver such that a presentation of the driver through the abdominal wall—or a guide channel provided in a cooperating device—will direct the anchor in the same direction as the leading end of the driver. The driver may extend through the anchor, in which case the driver will have a piercing leading surface that will extend beyond the body of the anchor and which on delivery of the anchor to the abdominal cavity can be withdrawn from the anchor, leaving the anchor in situ.

FIG. 3 shows how a driver 2200 may engage with an anchor 2100—such as the examples of FIG. 2 and then drive the anchor forwardly. As is shown, the driver 2200 engages with an end surface of the anchor. Pushing the driver forwardly effects a corresponding movement of the anchor through and into the abdominal cavity. In this arrangement the driver has a main body portion 2202 and a tapered end portion 2203. The tapered end portion 2203 has a smaller cross sectional diameter than the body portion 2202. In this way when the tapered end portion 2203 is presented into and engages with the end 2106 of the anchor, a step 2204 is formed. This step provides an abutment surface. When the anchor is delivered to the abdominal cavity and the driver is being withdrawn from the anchor, the abutment surface of the step 2204 will engage with or contact against the abdominal wall. This will create a resistance which facilitates the removal of the driver from the anchor. The outer diameter of the end portion 2106 in the region of the step is greater than the diameter of the tapered end portion 2203. It may extend to have a diameter as great as the diameter of the body portion 2202 of the driver.

In the arrangement of FIGS. 3A and 3B the driver projects through the anchor such that the anchor is located on the driver between the driver needle end portion 2205 and the main body 2202. The needle end portion is desirably sharpened to allow a piercing of the abdominal wall as necessary. The length of the needle end portion and geometry may vary—as shown in the examples of FIGS. 3A and 3B.

The end surface 2100 of the anchor may also include a chamfered outer surface 2207 which also facilitates the presentation of the anchor through the abdominal wall. It will be appreciated that as the driver is presented through the abdominal wall, the pressure on the leading surface 2207 will increase and will push the anchor towards the head of the driver, until such time as the inner diameter of the anchor is greater than the outer diameter of the driver, at which time movement rearwardly of the anchor is prevented.

FIG. 4 shows another example of an anchor and driver arrangement. The same reference numerals will be used for similar parts. Again, and similarly to that previously described, an anchor is located on a driver which is used to deliver the anchor within the abdominal cavity. In this arrangement, the needle end portion 2205 is not provided with a continuous tapered outer surface but rather is configured in a two part construct with a tip 400 being provided at the very end of the driver. The tip advantageously allows the anchor to be positioned on the non-tip portion such that the needle portion is never within the lumen of the anchor. In that scenario there would be an opportunity for tissue to lodge at the tip of the anchor and prevent accurate deployment of the anchor.

This arrangement of driver differs from that previously described in that it includes a cleat 405 or other securement feature. In this configuration the cleat is integrally formed in a head portion 410 of the driver. This is advantageous in that it allows the suture 2101 to be maintained in location along the body of the driver. It also ensures that an end portion of the suture is accessible subsequent to delivery of the anchor into the abdominal cavity. It will be appreciated that the actual location or form of the securement feature may vary.

The head portion 410 also includes a textured outer surface 415 which provides improved grip to the user of the driver. This may be formed in a variety of different ways such as overmoulding an elastomeric material onto the body of the driver.

Figure 5:
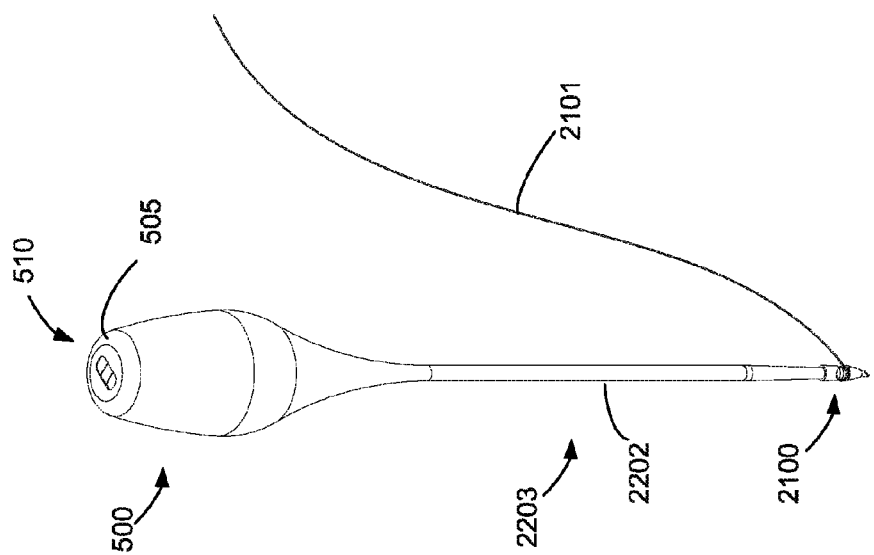
FIG. 5 is another example of a driver and anchor combination.

FIG. 5 shows another example of a driver which again uses the same reference numerals for parts previously described. In this configuration a bulbous head portion 500 is provided. This is another grip configuration that may be advantageously employed within the context of the present teaching. Use of such a bulbous head allows location of the driver securely into a user's palm and increases the amount of actual force that may be used in delivery of the anchor through the abdominal wall. Such an arrangement is particularly advantageous in scenarios where the driver is used by itself to effect presentation of the anchor through the abdominal wall.

In the absence of another guide structure to assist the surgeon or other operator in correctly identifying when the anchor has been delivered correctly, the present teaching provides a driver with an integrated guide indicator. An example of such an arrangement is shown in an upper surface 505 of the bulbous head 500. In this configuration a visual indicator 510 is provided. This configuration of the visual window employs three windows—although of course it will be appreciated that the dimensions or numbers of such windows may vary. The windows are colour coded and dependent on the orientation of the driver relative to the desired orientation one of the windows may be preferentially illuminated. For example, the driver may include an angular orientation sensor implemented in the form for example of an accelerometer or gyroscope, which will provide an output of the angular orientation of the driver relative to a predetermined plane. The driver may be pre-calibrated, or the surgeon may be able to calibrate the driver himself, as to a correct presentation angle. When the driver is presented to the abdominal wall at that angle—or within a predetermined range of that desired presentation angle—the window will show a first colour, for example green. When the driver orientation is slightly beyond that desired presentation angle, a second colour for example orange may be displayed. This will prompt the surgeon to modify the angle of presentation until the green is again shown. Where the angle is completely outside the preferred range a different colour, for example red, may be shown. This may prompt the surgeon to withdraw and retry. The visual indicators of green, orange and red are exemplary of the type of visual indicator that may be deployed. In addition or in replacement to such a visual indicator, the driver may include an audible warning generator which will be similarly activated dependent on the orientation of the driver relative to a desired preselected orientation. The necessary hardware and or software necessary to implement such an angular indicator may be located within the bulbous head of the driver.

Where the driver is used to directly pass the anchor through the abdominal wall it is preferable that the driver has a degree of rigidity such that it will not flex during the presentation to and through the abdominal wall. In other configuration where the driver is for example presented through a guide channel it may be necessary for all or part of the driver body to have a degree of resilience or flex to allow it adopt to the contours of the guide channel. These two forms of driver may be collectively known as rigid or flexible drivers and within the context of the present teaching it is not intended to limit to any one form of driver—except as may be deemed necessary in light of a specific application of use.

Figure 7:
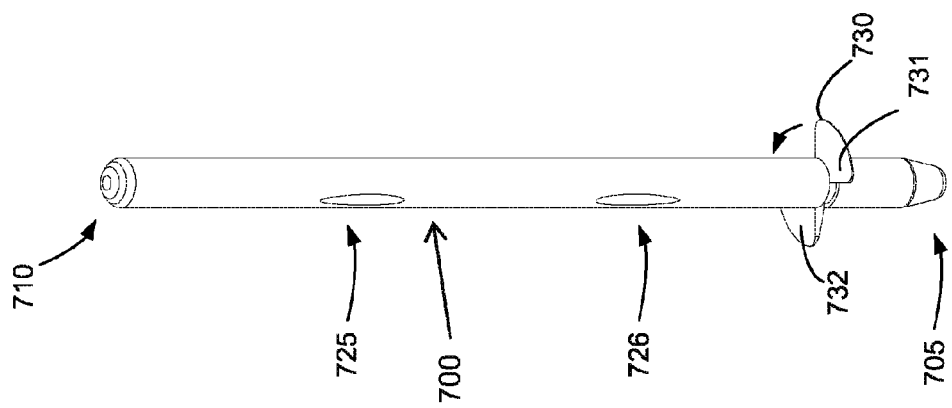
FIG. 7 is another example of a guide that may be used with the anchor and driver.
Figure 6:
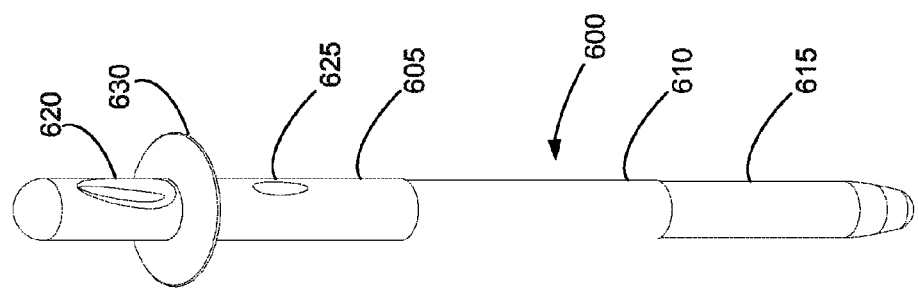
FIG. 6 is an example of a guide that may be used with the anchor and driver.

FIG. 6 and FIG. 7 show an example of a guide tool that may be used in combination with the driver/anchor arrangement heretofore described. In the example of FIG. 6 a guide 600 is provided. The guide is configured to define a driver guide channel located between an inlet 620 and outlet 625 defined within the body of the guide 600. In this exemplary configuration the body is provided in a telescopic arrangement comprising first 605, second 610 and third 615 parts. It will be appreciated that the number and dimensions of these parts may vary dependent on the actual implementation. The telescopic arrangement facilitates different defect or trocar lengths.

A flange 630 is provided between the inlet 620 and outlet 625. The flange 630 provides a collar which has a larger diameter than the body of the guide 600. In use the guide body 600 will be presented through a cut formed in the abdominal wall and will pass through that cut until the collar abuts against the outer part of the fascial layer. The collar provides a locator to assist the surgeon in ensuring the relative location of the outlet 625. The driver with attached anchor may then be presented through the inlet which is located outside the body and will pass out the outlet into the abdominal wall. It will be appreciated that in certain configurations the inlet and outlet will be on the same side of the guide 600. This will require the driver to have degree of flexibility sufficient to allow it to deform to the curved channel formed between the inlet and outlet.

In another configuration, the inlet and outlet are on opposing sides of the guide 600 such that a rigid driver may be presented through the inlet and along a substantially straight channel before exiting the outlet.

FIG. 7 shows another example of a guide 700 which differs in that a flange 730 is located in a lower portion of the guide 700. The guide has a leading end 705 and a trailing end 710. The flange is desirably flexible such that when the guide is being presented through the abdominal wall the flange will flex rearwardly away from the leading end 705 and attempt to conform with the contours of the body of the guide 700. To facilitate this conformity of the flange and ensure that it does not project substantially beyond the body surface during passage through the abdominal wall, it may be preferable not to form the flange as a continuous piece. In the example of FIG. 7, the flange is formed from two portions 731, 732 which are located on either side of the flange body.

During the passage of the body through the abdominal wall the flange portions 731, 732 will deform in the direction shown by the arrow so as to attempt to be parallel with the major axis of the body 700. On receipt within the abdominal cavity, there is no biasing force on the flange with the result that the flange portions will return to their normal position, which is substantially perpendicular to the body—the position shown in FIG. 7. In this way when a surgeon retracts the guide, the open flange will contact against an inner surface of the abdominal wall giving the surgeon tactile feedback as to the location of the guide.

This guide 700 also includes an inlet 725 and outlet 726. The inlet will, similarly to FIG. 6, be located outside the body and allows for the presentation of a driver into the guide. The driver and its associated anchor will then travel out of the outlet and into the abdominal wall. Further application of pressure onto the driver will cause the driver and anchor to pass into the abdominal cavity. Retraction of the driver will then release the anchor from the driver and the application of tension onto the suture will increase the tension applied onto the anchor and bring it into contact with an inner surface of the abdominal wall.

FIG. 8A shows the guide of FIG. 7 including a section line A-A. FIGS. 8B and 8C show two alternatives of guide channels that could be formed within the body of the guide.

In the example of FIG. 8B, a driver will enter a guide channel 800 on a first side of the body and then exit from a second side—shown in the two examples of a solid and dash line. Effectively first and second guide channels are provided. This arrangement is particularly usefully deployed in conjunction with a rigid driver as the channel 800 is substantially straight. The angle of the channel will determine the angle of presentation of the driver and associated anchor into the abdominal wall.

In the example of FIG. 8C the driver will enter and exit a guide channel 810 on the same side of the body. First and second channels 810 are provided on either side of the body and the driver will require a degree of flexibility to allow it to adopt to the curved contour of the channel 810. The driver will exit via the exit port 726 at an angle determined by the deflection surface 815 provided proximal to the exit 726.

FIG. 8D shows yet a further example which is not based on the configuration of FIG. 7. In this example, the entry ports are in the top of the body such that the driver will be presented coaxially with the major axis of the guide prior to being deflected outwardly by a deflection surface 815 provided proximal to the exit port 726.

Figure 10:
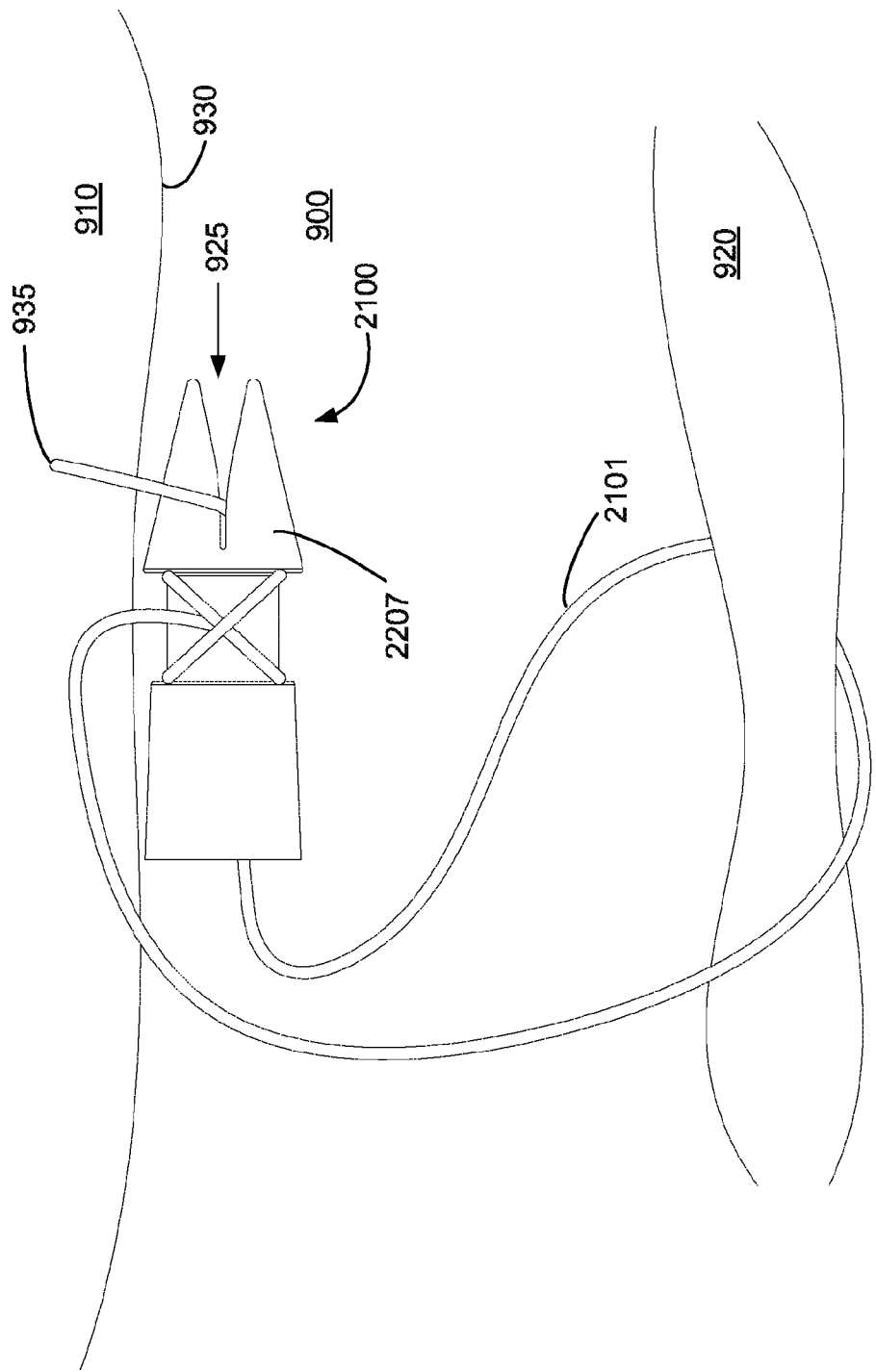
FIG. 10 shows an example of how an anchor may be used to effect movement of an organ in accordance with the present teaching.

FIGS. 9, 10 and 11 show examples of how an anchor in accordance with the present teaching may be used to assist in the moving of internal organs to allow a surgeon access to a surgical site. The schematics of these Figures illustrate the scenario where the anchor has already been deployed into the abdominal cavity. In these examples, the void 900 represents the abdominal cavity and the abdominal wall 910 is located above same. A representative organ—the small bowel 920—is shown as an example of the type of organ that may require movement to allow surgical access to a site otherwise occluded by its normal location.

In the examples of FIGS. 9 and 10 an anchor 2100 is secured to suture 2101 using a knot 2108—similarly to that described before. Suture is passed through the abdominal wall—such as using the technique that will be described below with reference to FIG. 11—and then looped around the organ to be moved. The suture may then be retained in the anchor using a cleat or other securement feature 925. It will be appreciated that the tensioning of the anchor against the abdominal wall 910 is achieved by tightening the suture until such time as the anchor 2100 is brought into contact with an inner surface 930 of the abdominal wall. A free end 935 of the suture may then be passed around the organ 920 and pulled so as to move the organ to a desired location. The securement of the suture within the cleat 925 maintains that desired location until such time as the surgical requirement for the movement of the organ is dispensed with, at which time the release of the suture from the cleat will allow the organ return to its normal location.

In the arrangement of FIG. 9, the cleat is provided or formed in the back end 2106 of the anchor. The cleat is formed by a cut 926 in the back end that extends from the step 2204 back to an eye 927. The suture may be passed through the eye—which defines an opening in the body of the anchor sufficiently large for the suture to pass—and then locked in the cut 926 where it is retained.

In the example of FIG. 10, the cleat is formed in the front end 2207 of the anchor 2100. The free end 935 of the suture is passed through the back of the anchor and through the body of the anchor where it is then secured in the cleat. Such an arrangement is advantageous as the suture cleat is adjacent to the suture and is provided in the form of a tapered slot which may provide a more secure attachment to that of FIG. 9 and thereby may be usefully employed for heavier organs.

FIG. 11 shows an example of how the suture shown in the abdominal wall of FIGS. 9 and 10 can be located. Desirably a tissue grasper 1100 which comprises two opposing arms 1105, 1106 which are moveable relative to one another is used to grasp a portion of the abdominal wall 910. Each of the arms include a window 1110 through which an anchor 2100 deployed on a driver 2200 may be presented. The anchor will therefore pass through the portion of the abdominal wall retained within the tissue grasper arms, and will bring its associated suture 2101 with it. Once through both surfaces a retraction of the driver will displace the anchor from the driver and allow for the subsequent looping of the suture about the tissue or organ that requires movement.

The grasper 1100 and driver 2200 may be activated externally of the abdominal cavity during laparoscopic surgeries.

The examples of the driver and anchor illustrated heretofore have described the suture running externally of the driver. In other configurations each of the anchor and driver may be configured to allow the suture to pass internally from the anchor through the body of the driver. The suture will then exit the driver from an exit port which is operably located externally of the body. Such an arrangement advantageously allows the surgeon to visualise the deployment of the suture and anchor as it is easier to see the suture passing relative to the exit port of the driver.

In other configurations—examples of which are described with reference to FIG. 12, the anchor and driver are co-operable with a guide shaft 1200. The guide shaft 1200 is desirably provided with a tapered or sharpened leading edge. The guide shaft may be used for transporting the anchor 2100 through the abdominal wall into the abdominal cavity—the anchor being located within the guide shaft during this passage. On passage of the leading edge 1205 into the abdominal cavity, the anchor 2100 may then be biased out of the guide shaft using a driver 1210. As the driver and anchor in these configurations do not have to come into contact with the abdominal wall during the transit of the anchor into the abdominal cavity, their shapes and configurations do not have to be contoured to facilitate such passage. For this reason, anchor configurations such as those shown in FIGS. 12C and 12D which have blunt as opposed to tapered or sharpened ends can be used. FIG. 12D also shows a variant in coupling of the suture to the anchor whereby a knot is located within the anchor as opposed to tied on the outer surface—such as FIGS. 12A to 12C. This arrangement of FIG. 12D is similar in construct to that described with reference to FIGS. 2A and 2B. FIG. 12E shows another variant whereby the driver is configured to receive suture within the body of the driver. In this way the suture is retained within the driver until such time as the driver is withdrawn from the surgical site, at which time the suture will be drawn out from the driver.

While the guide of FIG. 12 may be used independently of another guide, it is also possible to deploy the guide in conjunction with one or more of the guides described above with reference to FIG. 8. In such an implementation the anchor and driver are provided within a guide such as that shown in FIG. 12. A guide such as that shown in FIG. 8 is then deployed into the abdominal incision and provides a channel for delivery of the FIG. 12 guide to allow deployment of the anchor.

The guide shaft of FIG. 12 may also incorporate a flange or collar such as that described with reference to FIG. 7, which will assist the surgeon in determination when the guide shaft has pierced the abdominal wall and is in location for delivery of the anchor into the abdominal cavity. On location the anchor can be biased out of the guide shaft using an application of pressure via the driver 1210.

In a certain configuration the length of travel of the driver 1210 within the guide shaft may be limited so as to control how far the anchor is pushed relative to the end of the guide shaft. Such control is particularly advantageous in deployment of barbed suture such as that shown in FIG. 12B. In this arrangement a plurality of barbs 1215 are integrated onto the suture—examples include unidirectional and bidirectional barbs. As the barbs will naturally engage with the tissue that they contact it is important to control their deployment. In accordance with the present teaching the barbed suture may be contained within the guide shaft until such time as it is needed. The deployment may then be controlled.

An example of such control is where the driver is configured to have a length of travel just sufficient to bias the anchor out of the guide channel. In this scenario the anchor will then be hanging out of the guide, but the barbed suture will still be contained within the guide. Retraction of the guide by the surgeon will bring the anchor into contact with the abdominal wall where it will be retained. Continued retraction of the guide will then effect an exit of the barbed suture into the abdominal wall during the passage of the guide outwardly—the suture is actively deployed directly into the fascial layer. In such a configuration the barbs may advantageously be orientated opposite in direction to the anchor such that the barbs and anchor act in opposite directions to effect a securing in the fascial layers.

In the arrangements heretofore described the anchor and driver have been referenced with regard to a single deployment configuration. Effectively one anchor is provided onto the driver and then located as appropriate. The anchor is provided with a length of suture that can then be used to effect a closure of a wound or to provide an anchoring arrangement.

FIG. 13 shows a modification where there is a desire to retain or anchor a web, mesh, or organ at a plurality of locations.

In FIG. 13, the illustrated exemplary scenario is a desired retention of a web 1310 against the abdominal wall 1320. The web 1310 has an extended surface area and therefore requires retention at a plurality of locations. This is achieved in accordance with the present teaching by use of an anchor/driver combination. In this configuration an anchor 1330 is, similarly to that described before such as with reference to FIG. 2, coupled at a mid-point thereof to suture 1340. In such a configuration the anchor will hang vertically from the suture in an inverted T configuration—particularly if the point of coupling is the centre of gravity or center of mass of the anchor. In this configuration, which differs from the arrangements heretofore described, the anchor comprises first and second elements. The first element or main anchor body 1331 is similar to that described already. A second element, the anchor head 1332 is also coupled to suture but is coupled at the other end of the suture to the anchor body. In this way the suture 1340 separates the anchor head 1332 from the anchor body 1331.

Similarly to that described already, the driver 1315 is configured to engage with the anchor and to achieve a driving of the anchor to a desired location. In this arrangement, the driver comprises a socket 1316 provided in a leading end 1317 of the driver. This leading end 1317 may be sharpened or otherwise optimised to allow an at least partial penetration of the leading end of the driver into the abdominal wall or other organ as desired.

The anchor head 1332 is seatable in the socket 1316 and when seated, movement of the driver will effect a corresponding movement of the anchor 1330. In the example of FIG. 13, the driver will operably effect a driving of the anchor head into the abdominal wall 1320. The length of the suture 1340 separating the anchor head from the anchor body is desirably such that the length of travel of the driver into the abdominal wall is greater than the length of the suture. In this way when the driver effects a driving of the anchor into the abdominal wall, the anchor head will be driven into the actual abdominal wall whereas the anchor body 1331 which is trailing on the suture behind the anchor head 1332 will not travel into the abdominal wall. A compressive force is then applied between the delivered anchor head 1332 and the anchor body 1331 and this will achieve a retention of the anchor against the abdominal wall. By judiciously targeting the point of delivery of the anchor head, it is possible to locate a web or other material/device that requires anchoring between the anchor head and anchor body. In this way a located anchor serves to retain the web or other material/device in situ.

In certain configurations, one anchor may be sufficient. In other configurations—such as shown in FIG. 13, multiple anchors may be required. To facilitate this the anchor 1330 and driver 1315 may be provided in a gun configuration 1300 whereby a plurality of anchors may be sequentially used in conjunction with the same driver 1315. By bringing a succession of anchors into contact with the same driver it is possible to use that driver to locate, in a sequential fashion, a plurality of anchors which may be spring loaded in position or ratcheted into position.

In the arrangement of FIG. 13, the anchor and driver are located within the volume defined by a guide 1350. The guide comprises first 1351 and second 1352 walls and each of the anchors 1320 and driver 1315 are moveable relative to the walls of the guide.

A plurality of anchors are stacked or stackable in the guide. The anchors are desirably stacked such that the anchor head 1332 is located above the anchor body 1331. The orientation of the anchor body is desirably such that its major axis is parallel with the major axis of the guide. The head 1332 typically rests on a side surface of the anchor body 1331.

The driver is moveable between a resting and active position. In the resting position the socket 1316 is provided proximal to a head of a neighbouring anchor. The head 1332 may be displaced onto the socket 1316 by action of a pivotable actuator 1360 on the head 1332. This will typically be achieved by a triggering action effected by a user. The actuator 1360 comprises a chamfered surface 1361 which will, on movement of the actuator, displace the head 1332 into the path of the driver—where it is received and seated within the socket 1316. A second triggering action by the user will effect a movement of the driver out of the guide 1350. This is desirably achieved using a reciprocating spring motion or the like whereby the driver is driven with some force out of a mouth 1355 of the guide. As the head is seated in the socket and is also tethered to the body using the suture, this movement of the driver will effect a corresponding movement of the anchor out of the guide. The length of travel of the driver will determine the position of location of the anchor head. As discussed above, when the anchor head is located within the abdominal wall—or other desired location—a compression force is generated between the two which effects a securing of any material/device located between the two in situ.

The movement of a first anchor out of the guide will desirably effect a corresponding movement of the next anchor in line towards the mouth of the guide. In this way when the driver returns to its resting position, there is another anchor awaiting deployment within the gun.

The geometry of the anchor heads may vary dependent on the application. In the examples of FIG. 13, anchor heads are shown being a sphere, a tetrahedron, a cube and a dodecahedron but it will be appreciated that other configurations may also usefully be employed. It will be understood that the anchor heads can be provided as a molded part as could the suture element. In other configurations the anchor head could be formed from a knot formed in the suture or other material.

While preferred arrangements have been described in an effort to assist in an understanding of the teaching of the present invention it will be appreciated that it is not intended to limit the present teaching to that described and modifications can be made without departing from the scope of the invention.

It will be appreciated that the exemplary arrangements or examples of devices have been described with reference to the Figures attached hereto. Where a feature or element is described with reference to one Figure, it will be understood that the feature or element could be used with or interchanged for features or elements described with reference to another Figure or example. The person of skill in the art, when reviewing the present teaching, will understand that it is not intended to limit the present teaching to the specifics of the illustrated exemplary arrangements as modifications can be made without departing from the scope of the present teaching.

The words comprises/comprising when used in this specification are to specify the presence of stated features, integers, steps or components but does not preclude the presence or addition of one or more other features, integers, steps, components or groups thereof.

The invention claimed is:

1. A suture delivery system comprising:
    a hollow anchor having a longitudinal bore, the anchor being coupled to a suture extending circumferentially about the bore and in continuous contact with a recessed portion defined on the outer surface of the anchor, wherein the suture overlaps and is tied using a pre-tensioned constrictor knot located within the recessed portion such that the anchor is not moveable relative to the knot prior to delivery of the anchor into tissue;
    a driver, the anchor with the knotted suture coupled thereto being co-operable with the driver, the driver being dimensioned to be receivable through the bore of the anchor and terminating in a needle end portion which on cooperation of the driver with the anchor projects through and beyond the anchor bore, the anchor and driver being relatively dimensioned such that on receipt of the driver through the bore a step is defined between a trailing end of the anchor and the driver;
    wherein the driver is configured to allow an operator to operably apply pressure onto the anchor to affect delivery of the anchor into or through tissue and wherein on delivery of the anchor into or through tissue, the step defines an abutment surface with the tissue to effect a removal of the driver from the delivered anchor to leave the anchor in situ.

2. The system of claim 1 wherein the suture is coupled to the anchor at a midpoint thereof such that the anchor will hang from the suture in an inverted T configuration.

3. The system of claim 1 wherein the knot comprises a knot tail and wherein the knot tail is heat formed.

4. The system of claim 3 wherein the knot tail has an aglet.

5. The system of claim 1 wherein the suture is provided in a loop configuration through which a second anchor may be passed.

6. The system of claim 1 wherein the needle end portion is sharpened to allow a piercing of the tissue as necessary.

7. The system of claim 1 wherein the trailing end of the anchor engages with the needle driver.

8. The system of claim 7 wherein the driver has a main body portion and a tapered end portion, the tapered end portion having a smaller cross sectional diameter than the main body portion such that the step is formed when the tapered end portion of the driver is presented into and engages with the trailing end of the anchor.

9. The system of claim 8 wherein the abutment surface operably engages with or contacts against tissue and facilitates the removal of the driver from the anchor.

10. The system of claim 8 wherein an outer cross sectional diameter of the trailing end in the region of the step is greater than the cross sectional diameter of the tapered end portion.

11. The system of claim 7 wherein the anchor includes a chamfered outer end surface which also facilitates the presentation of the anchor through the tissue.

12. The system of claim 1 wherein the driver comprises a cleat.

13. The system of claim 12 wherein the cleat is integrally formed in a head portion of the driver.

14. The system of claim 1 wherein a head portion of the driver includes a textured outer surface which provides improved grip to the user of the driver.

15. The system of claim 1 wherein the driver comprises a bulbous head portion.

16. The system of claim 15 wherein the driver comprises an integrated guide indicator.

17. The system of claim 1 comprising a guide tool that is cooperable with the driver and anchor, the guide comprising a driver guide channel.

18. The system of claim 17 wherein the guide tool comprises an outlet whereby operably the anchor will exit the guide tool.

19. The system of claim 18 wherein the outlet is provided at an end of the guide such that the anchor will exit the guide within an abdominal cavity.

20. The system of claim 18 wherein the outlet is provided within a body of the guide such that operably the anchor will exit the guide and pass into an abdominal wall.

21. The system of claim 17 wherein the guide tool comprises a collar which facilitates locating of the guide relative to an abdominal wall.

22. The system of claim 17 wherein the guide tool comprises a sharpened end surface.

23. The system of claim 1 wherein the suture is barbed suture.

24. The system of claim 1 wherein the driver is hollow such that the suture may pass from the anchor through the driver.

25. The system of claim 1 wherein the anchor comprises an anchor body coupled to an anchor head via the suture.

26. The system of claim 25 wherein the driver comprises a socket configured to receive the anchor head.

27. The system of claim 25 comprising a guide within which the anchor and driver are locatable.

28. The system of claim 27 wherein the anchor and driver are moveable relative to the guide.

29. The system of claim 28 wherein movement of the driver out of the guide affects a delivery of an anchor to a desired location.

30. The system of claim 28 wherein the guide comprises an actuator configured to affect application of a force onto the anchor head to direct it into a socket of the driver.

31. The system of claim 27 wherein the guide is configured to receive a plurality of anchors, the guide comprising an actuator configured to sequentially deliver individual anchors into contact with the driver.

32. The system of claim 31 wherein the actuator affects movement onto the driver to deliver an anchor out of the guide.

33. The system of claim 1 wherein the suture is coupled to the anchor at the centre of mass of the anchor.

* * * * *